United States Patent [19]
Hildenbrand et al.

[11] Patent Number: 5,916,156
[45] Date of Patent: Jun. 29, 1999

[54] ELECTROCHEMICAL SENSORS HAVING IMPROVED SELECTIVITY AND ENHANCED SENSITIVITY

[75] Inventors: Karlheinz Hildenbrand, Krefeld; Hans-Ulrich Siegmund, Leverkusen, both of Germany

[73] Assignee: Bayer Aktiengesellschaft, Leverkusen, Germany

[21] Appl. No.: 08/798,387

[22] Filed: Feb. 7, 1997

[30] Foreign Application Priority Data

Feb. 15, 1996 [DE] Germany ............... 196 05 583

[51] Int. Cl.⁶ .................. G01N 27/327; C12Q 1/00
[52] U.S. Cl. ............ 600/347; 204/403; 422/82.03; 436/95
[58] Field of Search .................. 600/345, 347, 600/348, 355, 361; 204/403; 422/82.02, 82.03, 90; 436/73, 74, 95

[56] References Cited

U.S. PATENT DOCUMENTS

| | | | |
|---|---|---|---|
| 5,066,372 | 11/1991 | Weetall | 204/403 |
| 5,124,128 | 6/1992 | Hildenbrand et al. | |
| 5,130,009 | 7/1992 | Marsoner et al. | |
| 5,385,846 | 1/1995 | Kuhn et al. | 204/403 |
| 5,525,511 | 6/1996 | D'Costa | 204/403 |

FOREIGN PATENT DOCUMENTS

| | | |
|---|---|---|
| 0 078 636 A1 | 5/1983 | European Pat. Off. |
| 0 127 958 A3 | 12/1984 | European Pat. Off. |
| 0 276 782 A2 | 8/1988 | European Pat. Off. |
| 0 289 265 A2 | 11/1988 | European Pat. Off. |
| 0 351 891 A2 | 2/1990 | European Pat. Off. |
| 0 471 986 A2 | 2/1992 | European Pat. Off. |
| 0 546 536 A1 | 6/1993 | European Pat. Off. |
| 20 21 285 | 11/1971 | Germany. |
| WO 94/27140 | 11/1994 | WIPO. |
| WO 95/10223 | 4/1995 | WIPO. |

OTHER PUBLICATIONS

Sasso et al., Electropolymerized 1,2–Diaminobenzene as a Means To Prevent Interferences and Fouling and To Stabilize Immobilized Enzyme in Electrochemical Biosensors, Anal. Chem. 1990, 62, 1111–1117.

Primary Examiner—Michael Peffley
Assistant Examiner—Eric F. Winakur
Attorney, Agent, or Firm—Sprung Kramer Schaefer & Briscoe

[57] ABSTRACT

The present invention describes electrochemical sensors, preferably electrochemical biosensors, in which the reference electrode and the measuring electrode are separated from one another by a porous, electrically nonconductive sheet material.

9 Claims, 1 Drawing Sheet

ELECTROCHEMICAL SENSORS HAVING IMPROVED SELECTIVITY AND ENHANCED SENSITIVITY

BACKGROUND OF THE INVENTION

1. Field of the Invention

The present invention describes electrochemical sensors, preferably electrochemical biosensors. In addition, a method for fabricating electrochemical, preferably amperometric biosensors for the diagnostics of bodily fluids is described.

2. Description of Related Art

The use of amperometric biosensors, particularly in blood sugar diagnostics, has formed part of the prior art for some years.

Such products are described, for example, in U.S. Pat. No. 4,545,382, in EP 127 958, EP 351 891 and EP Appl. 0 47 1 986. The corresponding test systems are commercially available under the product names MediSense®, ExacTex® and Glucocard®. They permit a simple blood glucose diagnosis under home-user conditions.

Particular significance has been gained by the amperometric biosensors containing glucose oxidase as a receptor component. As described in detail in Anal. Chem. 1990, 62, 1111 to 1117, the reaction of glucose with glucose oxidase produces an amount of hydrogen peroxide which is proportional to the sugar concentration.

Since, however, the anodic oxidation $H_2O_2 \rightarrow O_2 + 2H^+ + 2e^-$ requires a relatively high cell voltage (approximately 600 mV), the analysis of whole blood may entail undesirable interference problems. This is because, at the above-mentioned voltage, certain blood components such as ascorbic acid likewise react, resulting in false positives.

Consequently, with a view to improving the selectivity of amperometric sensors, the idea of mediators has been developed. Frequently used mediators in the case of so-called second-generation biosensors are, for example, ferrocenes or potassium hexacyanoferrate $K_3Fe(CN)_6$. The amperometric blood glucose determination in this case proceeds according to the following reaction scheme:

(1) glucose+GO(FAD)→gluconolactone+GO(FADH$_2$)

(2) GO(FADH$_2$)+Fe(III)(CN)$_6^{3-}$→Fe(II)(CN)$_6^{4-}$+GO(FAD)+H$^+$ (3) Fe(II)(CN)$_6^{4-}$→Fe(III)(CN)$_6^{3-}$+e$^-$

The amperometric blood glucose determination is therefore confined, as far as measurements are concerned, to the anodic oxidation described under (3), which proceeds at a potential of +360 mV. Such mediator-modified biosensors thus have enhanced selectivity.

With a view to reproducible results, the O$_2$-controlled side reaction GO (FADH$_2$)+O$_2$→GO (FAD)+H$_2$O$_2$ must be prevented as far as possible.

The design of a suitable testing means includes, in addition to the necessary detection reagents, for example glucose oxidase and potassium hexacyanoferrate, at least two electrodes (working electrode and reference electrode), which must be in contact with one another via an electrolyte bridge.

Possible electrode materials according to the prior art are noble metals such as palladium, platinum, gold, silver and copper, or graphite, the anode (working electrode) and cathode (reference electrode) optionally being fabricated from different materials or from the same material and optionally having surfaces of equal or different size.

The test procedure in the case of the commercially available systems is confined, as far as the patient is concerned, to feeding in the liquid sample (whole blood), the analysis value being displayed digitally within at least one minute.

The actual course of the reaction, however, which involves oxidation of the analyte (glucose) and reduction of the mediator, is controlled in such a way, in terms of measurement, that the following steps are observed:

a) Blood is fed in and reaction proceeds according to (1) to (2).

b) After a certain reaction time of approximately 5 to 30 sec is observed, a constant voltage of approximately 400 mV is applied and the anodic oxidation described in (3) takes place.

c) After a short delay time the current is measured.

Analytic evaluation takes place within the range of diffusion-controlled limiting currents, the so-called Cottrell equation

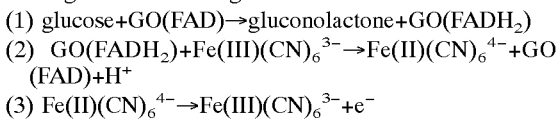

$$i(t) = \frac{n°F°A\sqrt{D°C}}{\sqrt{\pi}\sqrt{t}}$$

equation (A)

applying.

i=Current n=Number of electrons involved in the electrode reaction

F=Faraday constant

D=Diffusion coefficient

C=Concentration of the analyte

A=Area of the working electrode

D=Thickness of the diffusion boundary layer at the working electrode t=Time

If these conditions are to be met, the oxidized form of the redox mediator (K$_3$Fe(CN)$_6$) at the counter electrode must significantly exceed the concentration of the reduced mediator form (K$_4$Fe(CN)$_6$) at the working electrode.

Testing means which allow for separate application—involving, if required, fixing by immobilization—of the mediator system, for example potassium hexacyanoferrate (K$_3$Fe(CN)$_6$), to the counter electrode and of the enzymatic receptor (GO) to the working electrode should correspondingly provide an advantage.

Test systems containing separated reagent zones may also be advantageous with a view to long-term stability of the enzymatic reagent system.

A number of various publications list further desirable characteristics for electrochemical biosensors, which may contribute to an optimization, of the overall system.

Some important ones are listed below:

Further enhancement of the selectivity

Europ. Pat. Spec. 0 276 782 describes enzyme electrodes containing albumin layers cross-linked by glutardialdehyde, which, owing to their permeability, protect the working electrode against electroactive interfering components, particularly against proteins having a higher molecular weight.

The use of synthetic membranes to exclude the erythrocytes in the case of electrochemical cells is described in Europ. Pat. Appl. 0 289 265.

WO 94/27140 describes electrochemical sensors provided with erythrocyte exclusion membranes which contain mobile erythrocyte agglutinants.

Europ. Pat. Appl. 0 546 536 describes a system comprising a bipartite working electrode consisting of an enzyme-free and an enzyme-containing field, the former detecting oxidizable interfering components which cannot be reacted enzymatically, such as ascorbic acid. The corrected actual blood glucose level is then determined by means of calculation from the measurements of individual potentials.

Nankai et al. describe, in WO 86/07 642, a three-electrode system which, in addition to working electrode and reference electrode, also contains a comparison electrode which compensates for the dependence of cell voltage on the cell current.

Increase in the sensor sensitivity

The enhancement of the sensitivity by enlarging the electrode surface areas in line with equation (A) is described in EP 0 385 964.

Improved handleability

Nankai et al. describe, in Eur. Appl. 0 471 986, the fabrication of an amperometric blood glucose test system containing expendable sensors, said system being distinguished by particularly good handleability. The expendable sensor plugged into the amperometric analyser is made to touch, by the sensor tip, the drop of blood to be analysed. Via a microcapillary (capillary flow system) whole blood is conveyed into the sensor's working chamber (working electrode and reference electrode plus detection reagents). In the process, the detection reagents ($GO/K_3Fe(CN)_6$) dissolve in the liquid (blood) to be analysed, and the previously quoted detection reaction proceeds. If both electrodes are wetted with blood—a precondition for troublefree operability—the reduced resistance value automatically causes the analyser to start. The instrument can therefore be operated without any control buttons. With a view to extracting blood without undue pain, the amount of blood required is kept as low as possible and the volume of the microcapillary system is therefore restricted to approximately 5 $\mu$l. From the reaction chamber defined by the microcapillary conductor tracks lead, via the extended sensor section, to the plug-in contacts, any contamination of important functional components in the analyser thus being precluded.

The fabrication of the blood glucose biosensors quoted customarily makes use of a screen printing technology method.

The printing process of the electrode part (transducer) employs commercially available screen printing pastes, for example based on graphite or silver (Acheson), which are printed onto substrate materials such as ceramic or plastic sheets. This requires a number of successive printing and drying steps (conductor tracks, working electrodes, reference electrodes, dielectric layers).

The screen printing pastes which, with a view to workability, contain a number of different additives such as antifoaming agents, thixotropic agents and detergents, often exhibit significant deficiencies in terms of reproducibility.

Frequently, the screen-printed electrode surfaces still have to be activated by plasma treatment. This is because, owing to the high, relatively hydrophobic binder fraction, the surfaces tend to be hydrophobic, poorly wetted and have a markedly reduced conductivity compared with the pure conductor material, for example graphite or silver.

Further drawbacks of the plasma treatment such as ageing or generatinguesirable redox-active surface groups must be taken into account. Fabrication of the electrode part is followed by application of the detection reagent formulation, for example glucose oxidase (GO) and potassium hexacyanoferrate in the case of blood glucose detection. This requires each individual sensor working surface to be doped individually, either the screen printing technology method or the laborious method of micropipetting being employed.

In a third procedure, the microcapillary system is finally applied by bonding appropriately preformed sheets which, if required, have to be provided with hydrophilic layers with a view to good wettability.

Overall this is therefore a relatively complicated fabrication process.

SUMMARY OF THE INVENTION

Surprisingly, a method for fabricating electrochemical sensors has now been found, which is significantly simpler in terms of fabrication and is more reliable in terms of reproducibility.

In particular, the method according to the invention permits the combination, in one system, of those characteristics aimed for and described in the text, which should result in an improved product. In the prior art, said combined and integral profiles of characteristics have not yet been achieved.

Thus an enhancement of the sensitivity is possible in a simple manner by enlarging the reagent matrix area, without a significant increase in the sample volumes (e.g. drops of blood), as in the case of the conventional system, being required.

An increase in selectivity is possible by integrating porous separating layers. The fact is that, as described hereinafter in more detail, it is possible to integrate selectivity-enhancing separation processes in different sensor layers, for example porous reference electrode, membranes as a reagent matrix and possibly via membrane coating of the working electrode.

BRIEF DESCRIPTION OF THE DRAWINGS

The invention will now be described in further detail with reference to the drawing wherein.

DETAILED DESCRIPTION OF THE PREFERED EMBODIMENTS

Figure 1A:
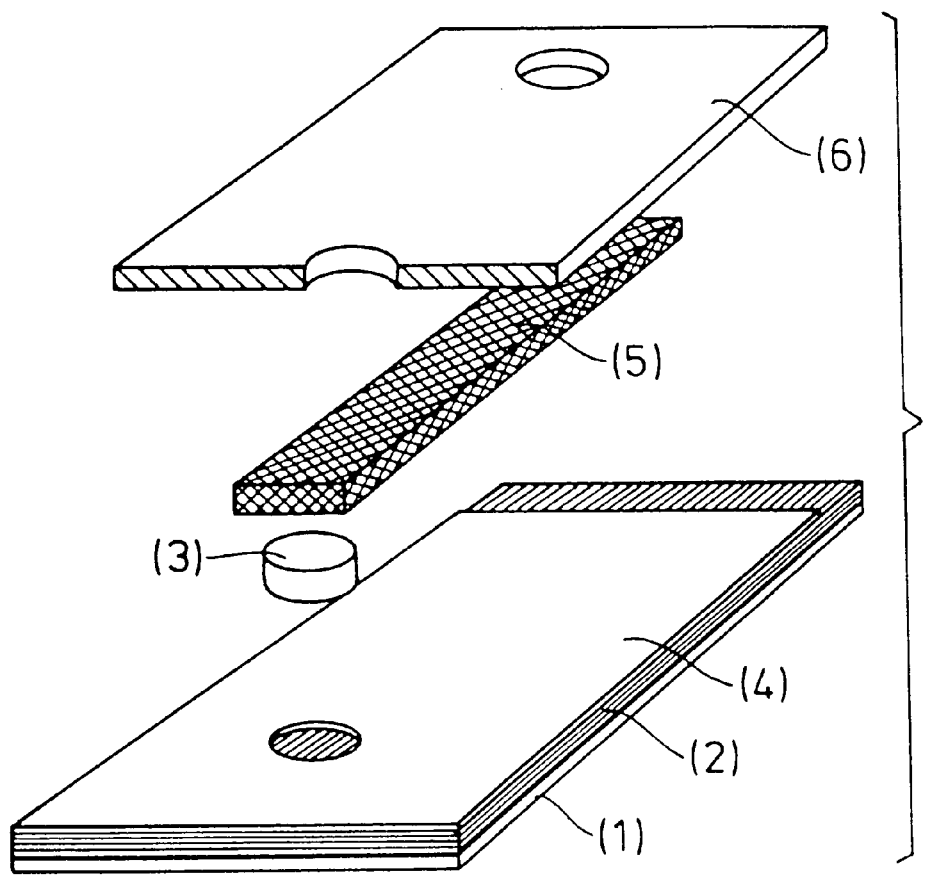
FIG. 1 is an illustration of an amperometric testing device according to the present invention.
Figure 1B:
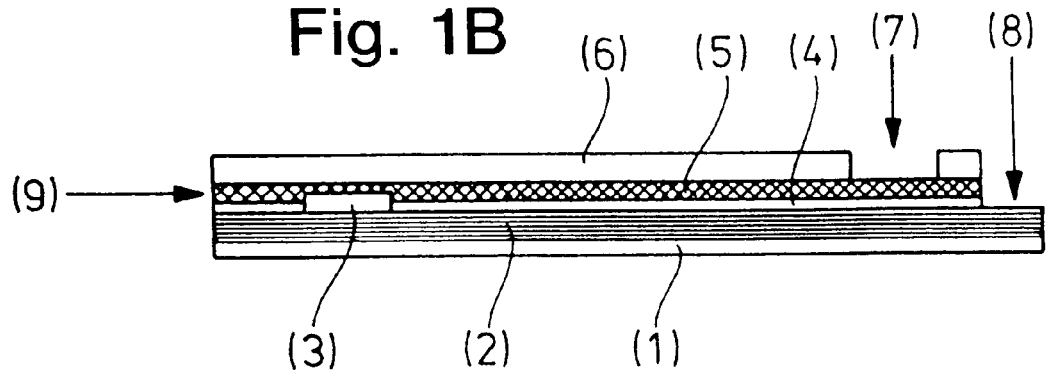

FIGS. 1A and 1B are intended to illustrate the sensor systems according to the invention:

Onto a graphite sheet (2) which is fixed to a base sheet (1) a reagent matrix (membrane) (3) having an area in the range of a few $mm^2$ is applied. On top of this a strip of a graphite web (5) is fastened by means of a perforated double-sided adhesive tape (4). Finally, a perforated sheet (6) is bonded on as a top covering. The sample volume required can be defined by integrating a liquid stop zone (10) in the graphite web, for example behind the reagent membrane (3).

Contact with a potentiostat is established at (7) to the graphite web layer (reference electrode, cathode) and at (8) to the graphite sheet (working electrode, anode). The sample can be fed in via the front edge (9) of the graphite web, entailing—as described in the examples—liquid being transported in the direction of the reagent matrix.

The components employed or possible for the individual functional layers are described below in more detail:

a) Working electrode

Preferably use is made of graphite sheets which are available under the brand name Sigraflex® from SOL Carbon Group.

The important characteristics for this intended purpose are:

electric resistivity: 8 to 10 $\Omega$ $\mu$m parallel to the layer 600 to 650 $\Omega$ $\mu$m perpendicular to the layer layer thickness: 0.25 to 1.00 mm purity: >99.85%

With a view to increasing the reaction selectivity it is possible, as will be described later in the examples, for the graphite surface which faces the reagent matrix (3) to be provided with an integral membrane layer which may either be a microporous pore membrane or a nonporous swellable membrane layer.

As an alternative to graphite sheets it is possible to employ other known electrode materials such as gold, silver or platinum.

A plasma treatment to improve wettability or to enhance the conductivity is unnecessary.

b) Porous base matrix

Porous sheet materials of possible use in this context can be selected from the group consisting of polymer webs, for example made of polyester or poly(vinyl alcohol), polymer wovens, for example made of polyamide or polyester, or preferably from the group consisting of polymer membranes.

Preferred polymer membranes are those which are associated with the microfiltration group and are within the pore range of from approximately 0.1 to 10 μm, particularly preferably in the range of from 0.3 to 5 μm and are distinguished by good wettability. Relevant examples are polyamide membranes (Biodyne®) from PALL, hydrophilized poly(vinyl fluoride) membranes (Durapore®) from Millipore, hydrophilized polysulphone membranes (Supor®) from Gelmann, or polymer blend membranes as described in U.S. Pat. No. 5,124,128.

The membrane types used can be self-supporting or supported on a base, with the options of the base material comprising polymer web or polymer woven and being integrated centrally or on one side into the membrane layer. In terms of structure, the membranes employed can be asymmetric or symmetric.

A particular advantage of the sensors according to the invention derives from the dual character of these special reagent matrices, which may have both reagent support functionality and separation functionality.

The choice of the most suitable porous base matrix depends on the specific application. Particularly good utility for the blood glucose test, for example, is provided by those membranes which readily allow plasma to permeate but retain the erythrocytes.

Alternatively, base matrix systems can be used which allow immobilisation of the detection reagents, for example glucose oxidase. Conceivable embodiments in that case would be, for example, continuously operating or reusable biosensors.

With a view to multistage detection reactions, for example cholesterol test, it is alternatively possible to combine a plurality of base matrix systems on top of one another. This then results in multifarious possibilities regarding incorporation of the detection reagents and for the purpose of removing undesirable interfering components.

As described below in slightly more detail, using the blood glucose test as an example, even in the case of single-layer matrix versions compared with screen printing or micropipetting, reagents can be incorporated in various ways which are of interest, for example, with a view to reaction performance or long-term stability: In the simplest case, the base matrix may be impregnated via conventional impregnation procedures, for example with a glucose oxidase and potassium hexacyanoferrate.

Alternatively it is possible for one or both sides of the matrix to be coated with a paste-like reagent preparation, with the additional option of combining impregnation and coating procedures.

Thus, for example, as described in detail in the examples the base matrix, in a preferred procedure for the amperometric blood glucose test, is impregnated with potassium hexacyanoferrate, while a paste-like glucose oxidase formulation is applied to the side facing the working electrode.

With all forms of reagent incorporation it is evident, however, that compared with methods such as screen printing or micropipetting it is possible rather than conventional methods established in test strip diagnostics individual sensor doping, resulting in considerable production advantages.

The reagent matrix areas used for the individual sensor can likewise be varied within a relatively wide range. If it is possible, for example, with analytes which are less sensitive or are in a relatively low concentration range, to employ larger reagent matrix areas in order to generate, according to equation (A), close response signals which can still be readily interpreted, without disproportionally large sample volumes (for example blood) being required.

Because of the option being able to increase the sensitivity via the reagent matrix area the sensors according to the invention are, in particular, also of great interest for immunochemical detection systems.

Practicable matrix areas are in the range of a few $mm^2$. As described in the examples, evaluation of the blood glucose test made use of circular matrix discs having a diameter of 3 mm, corresponding to an area of approximately 7 $mm^2$.

Surprisingly, the biosensors fabricated therewith were able to function with sample volumes in the range of no more than about 2 μl, and it was possible, compared with the previously known blood glucose biosensors, to achieve distinctly higher current yields (values increased approximately eightfold).

Conventional biosensors comprise working electrode areas of approximately 1 to 2 $mm^2$, require volumetric amounts of sample (blood) of at least 5 μl and achieve a current yield in the range of from approximately 0.1 to 20 μA.

Sensor systems which are able to function with minimal sample volumes are of interest in particular in the context of the so-called "minimal invasive" designs (PCT WO 95/10223), values of 2 μl or less being aimed for.

Porous, conductive reference electrode

The preferred material employed comprises, as mentioned previously, graphite webs which can be obtained, for example, under the brand name Sigrafil® SPC 7011 from SGL Carbon Group.

These are black, highly tear-resistant webs having a mass per unit area of 30 $g/m^2$, a thickness of 0.5 mm, a mean fibre diameter of 7 μm and a binder system of crosslinked poly(vinyl alcohol) with a percentage of approximately 20 to 24 wt %.

As previously indicated, this material is distinguished by two special characteristics which are of particular interest for the fabrication of electronic biosensors. These are the capability for very rapid and nondestructive transportation of liquid both in a vertical and a horizontal direction, and its electrical conductivity, the electrical resistivity being in the region of approximately 10 Ω μm.

This graphite web layer can thus perform, at the same time, the function of the capillary transport of liquid and that of the reference electrode.

Such graphite web layers in conjunction with agglutinants such as lectins can also, in an eminently effective manner, achieve a blood/plasma separation.

Such separation processes are of considerable interest in the analysis of blood samples with a view to reducing the influence of the haematocrit.

Alternatively it is possible to use, instead of the graphite webs mentioned, other electroconductive porous sheet materials such as metallized wovens, webs or membranes, which can be treated with surface-active substances to improve wettability.

An example of a suitable electroconductive woven to be mentioned is the type Metalen 120 bis 34 T from SEFAR.

This is a nickel-coated multifilament polyester woven.

Conductive membranes can be obtained, for example, from Millipore, based on pure silver.

This objective of the conductive, porous reference electrode can also be met by using conventional membranes which have been metallized in accordance with one of the common processes.

d) Plastic sheets

The base sheet (1) or the top covering sheet (6) may, in principle, be chosen from the large range of plastic sheets, without a major selection procedure.

With a view to the mechanical stability of the biosensor strip preference is given, however, to sheets having certain stiffnesses and layer thicknesses.

Use has been made, for example, of polyester sheets, polycarbonate sheets and PVC sheets in the thickness range of from approximately 100 to 300 $\mu$m, which, in part, were transparent or pigmented.

With a view to an improved transport of liquid it may be advantageous for the inside of the covering sheet to carry a hydrophilic support layer. Sheets thus modified can be found, for example, in the standard sheet range of ICI or Du-pont.

The bonding or laminating of the individual layers can be carried out, as mentioned, with the aid of adhesive tapes, hot melt adhesives or one of be known welding methods.

Example

An amperometric testing means according to FIG. 1 was constructed:

(1) Base sheet (Polycarbonate sheet, thickness 250 $\mu$m)
(2) Graphite sheet (Sigraflex®, fastened onto (1) with double-sided adhesive tape)
(3) Reagent membrane (Biodyne® from PALL, impregnated with glucose oxidase and potassium hexacyanoferrate)
(4) Double-sided adhesive tape
(5) Graphite web (Sigratex® SPC 7011)
(6) Covering sheet (Polycarbonate sheet, 250 $\mu$m thick)

Contact with the amperometer was established to the graphite web at (7) (cathode, reference electrode) and to the graphite sheet at (8) (anode, working electrode).

The sample (3 $\mu$l) was fed in at the front side (9) of the graphite web with the aid of a pipette, resulting in a capillary transport of liquid in the direction of the reagent matrix.

Preparation of the reagent matrix:

a) Impregnation with potassium hexacyanoferrate

A nylon membrane from PALL (Biodyne, 0.45 $\mu$m) was impregnated with a 20% strength potassium hexacyanoferrate solution and dried.

b) Incorporation of glucose oxidase

With the aid of a high-speed stirrer (dissolver) a coating solution containing glucose oxidase was prepared from the following components:

4.42 g Polyethylene oxide 300,000 (Union Carbide)
84.08 g Citrate buffer (0.01 molar, pHt is 6.5)
0.58 g Octan-1-ol
3.84 g Aerosil® (highly disperse silicic acid from Degussa)
0.12 g Surfactant FC-170 C (from 3M)
7.00 g Glucose oxidase (150 $\mu$/mg)

After degassing, this coating solution was applied, with the aid of a doctor knife (wet application 50 $\mu$m) to the nylon membrane impregnated with potassium hexacyanoferrate and dried with warm air.

With the aid of a revolving punch, circular discs having a diameter of 3 mm were punched from the reagent membrane thus prepared.

After the design shown in FIG. 1 had been set up, amperometric test series were carried out at 400 mV with the following test solutions:

a) Aqueous standard solutions
0, 25, 50, 100, 200, 300, 400, 500 mg/dl glucose

Measuring times of 30 sec were observed, chronamperometric curves being obtained which descended with 1/t in accordance with the Cottrell equation. As the glucose concentration increased, values with increasingly higher current densities were obtained.

b) Whole blood

Fresh whole blood with a glucose level of 104 mg/dl was applied in analogy to a). This resulted in a measured curve which largely coincided with the 100 mg/dl curve from a).

2. Example

Preparation of membrane-coated graphite sheets a) Porous membrane layer

With the aid of a high-speed stirrer (dissolver) a coating solution was prepared from the following components:

| Dralon L | (Bayer AG) | 50.0 g |
| Ultrason E | (BASF) | 50.0 g |
| Aerosil 200 | (Degussa) | 30.0 g |
| Pluriol P 600 | (BASF) | 90.0 g |
| N-methylpyrrolidone | (NMP) | 484.0 g |

After degassing, this coating solution was applied, with the aid of a doctor knife (wet application 150 $\mu$m) to a graphite sheet (Sigraflex) and immersed in a water bath. After drying and impregnation with glucose oxidase and potassium hexacyanoferrate a membrane disc with a diameter of 3 mm was punched out, as described in Example 1, and the design likewise described in Example 1 was set up.

In the course of chronamperometric analysis, increasing current densities were obtained with increasing glucose concentrations, in analogy to Example 1a.

b) Nonporous, swellable membrane layer on graphite sheet

With the aid of a high-speed stirrer a casting solution was prepared from the following components:

| 8.77 g of aqueous polyurethane dispersion DLS | (Bayer AG) |
| 9.66 g of polyethylene oxide 300,000 | (Union Carbide) |
| 0.06 g of pluronic PE 6,400 | (BASF) |
| 1.20 g of citrate buffer (0.1 m, pH = 6.5) | |
| 0.34 g of Aerosil 200 | (Degussa) |
| 1.00 g of glucose oxidase (154 U/mg) | |

After degassing, this coating solution was applied, with the aid of a doctor knife (wet application 100 $\mu$m) to a graphite sheet (Sigraflex®), dried and punched out (circular disc 3mm).

The working electrode thus coated was used according to (3), FIG. 1. In the course of the evaluation using aqueous glucose solutions, with an applied voltage of 600 mV, increasing current intensities are measured with increasing glucose concentrations, in analogy to Example 1a.

Results of the glucose sensors comprising membrane-coated graphite sheets:

Whereas pure, aqueous glucose solutions produced results largely analogous to those in Example 1, the membrane-modified sensor systems gave better results with respect to test solutions which also contained interfering components (ascorbic acid, acetaminophen).

A false-positive change due to the interfering compound had been virtually completely eliminated.

We claim:

1. An amperometric testing device comprising a working electrode and a reference electrode, wherein said working electrode is separated from said reference electrode by an electrically non-conductive sheet material, said electrically non-conductive sheet material comprises a plurality of individual layers, and the individual layers comprise different reagents.

2. An amperometric testing device according to claim 1, wherein the electrically non-conductive sheet material comprises a porous material.

3. An amperometric testing device according to claim 2, wherein said porous material is selected from the group consisting of polymer web materials, polymer woven materials and polymer membranes.

4. An amperometric testing device according to claim 1, wherein said reference electrode comprises a sample reaction zone, wherein said sample reaction zone comprises an electroconductive nonwoven or web material that is capable of capillary transport of liquid.

5. An amperometric testing device according to claim 4, wherein said electroconductive nonwoven or web material comprises a hydrophilic graphite fiber material.

6. An amperometric testing device according to claim 5, wherein said hydrophilic graphite fiber material is a graphite nonwoven material.

7. An amperometric testing device according to claim 4, wherein said electroconductive nonwoven or web material comprises a nonconductive hydrophilic nonwoven material overlaid with a conductive metal or graphite sheet.

8. In a diagnostic assay method comprising analyzing a sample with an amperometric testing device, wherein the improvement comprises using as the amperometric testing device an amperometric testing device according to any one of claims 1–7.

9. A method according to claim 8, which is a blood sugar diagnostic assay method.

* * * * *